United States Patent
Vogt et al.

(10) Patent No.: US 8,973,521 B2
(45) Date of Patent: Mar. 10, 2015

(54) COATING DEVICE AND COATING METHOD

(75) Inventors: Sebastian Vogt, Erfurt (DE); Hubert Büchner, Nürnberg (DE)

(73) Assignee: Heraeus Medical GmbH, Wehrheim (DE)

( * ) Notice: Subject to any disclaimer, the term of this patent is extended or adjusted under 35 U.S.C. 154(b) by 387 days.

(21) Appl. No.: 13/332,703

(22) Filed: Dec. 21, 2011

(65) Prior Publication Data

US 2012/0164310 A1    Jun. 28, 2012

Related U.S. Application Data

(60) Provisional application No. 61/432,792, filed on Jan. 14, 2011.

(30) Foreign Application Priority Data

Dec. 23, 2010  (DE) .......................... 10 2010 055 562

(51) Int. Cl.
| | |
|---|---|
| *B05C 1/00* | (2006.01) |
| *A61L 27/54* | (2006.01) |
| *B05C 1/06* | (2006.01) |
| *A61L 31/16* | (2006.01) |

(Continued)

(52) U.S. Cl.
CPC . *A61L 27/54* (2013.01); *B05C 1/06* (2013.01); *A61L 31/16* (2013.01); *B05D 1/28* (2013.01); *A61L 2300/406* (2013.01); *A61L 2420/02* (2013.01); *B05C 17/00* (2013.01)
USPC ............... 118/264; 118/267; 118/270; 604/1; 604/2; 604/3

(58) Field of Classification Search
CPC ....... A61M 35/006; B65D 47/42; B05C 1/06; B05D 1/28; A61L 27/28; A61L 27/54; A61L 31/16; A61L 31/08; A61L 2300/406; A61L 2420/02
USPC ........... 118/264–268; 604/1–3; 401/132–135, 401/139; 132/320, 317, 318, 218
See application file for complete search history.

(56) References Cited

U.S. PATENT DOCUMENTS

| | | | |
|---|---|---|---|
| 4,563,324 A | | 1/1986 | Kubat et al. |
| 5,490,736 A | * | 2/1996 | Haber et al. .................... 401/40 |
| 5,607,685 A | | 3/1997 | Cimbollek et al. |

(Continued)

FOREIGN PATENT DOCUMENTS

| | | |
|---|---|---|
| DE | 4404018 A1 | 8/1995 |
| DE | 10142465 A1 | 7/2003 |

(Continued)

OTHER PUBLICATIONS

Office Action issued Jul. 6, 2011 in DE Application No. 10 2010 055 562.2.

(Continued)

*Primary Examiner* — Laura Edwards
(74) *Attorney, Agent, or Firm* — Pantich Schwarze Belisario & Nadel LLP

(57) ABSTRACT

A device for coating a medical implant includes a container that contains a liquid having at least one pharmaceutically active substance. An elastic head for application of the liquid onto a surface to be coated is connected to an inside of the container through at least one channel.

13 Claims, 2 Drawing Sheets

(51) Int. Cl.
*B05D 1/28* (2006.01)
*B05C 17/00* (2006.01)

(56) References Cited

U.S. PATENT DOCUMENTS

| | | | |
|---|---|---|---|
| 5,679,646 | A | 10/1997 | Cimbollek et al. |
| 6,423,550 | B1* | 7/2002 | Jenkins et al. ............... 436/518 |
| 7,030,093 | B2 | 4/2006 | Vogt et al. |
| 7,563,324 | B1 | 7/2009 | Chen et al. |
| 2005/0031664 | A1 | 2/2005 | Vogt et al. |
| 2006/0029722 | A1 | 2/2006 | Larson et al. |
| 2007/0125247 | A1 | 6/2007 | Kunstmann et al. |
| 2007/0196817 | A1* | 8/2007 | Broom ............................. 435/5 |
| 2007/0253761 | A1* | 11/2007 | May ............................. 401/133 |
| 2007/0281072 | A1 | 12/2007 | O'Connor et al. |
| 2008/0003052 | A1* | 1/2008 | Lee et al. ...................... 401/209 |
| 2008/0206442 | A1 | 8/2008 | Shekalim et al. |
| 2008/0260936 | A1 | 10/2008 | Heidner et al. |
| 2009/0024096 | A1* | 1/2009 | Hai et al. ...................... 604/265 |
| 2010/0179475 | A1* | 7/2010 | Hoffmann et al. ....... 604/103.02 |
| 2011/0287169 | A1 | 11/2011 | Hoffmann et al. |
| 2012/0259290 | A1 | 10/2012 | McDermott et al. |

FOREIGN PATENT DOCUMENTS

| | | |
|---|---|---|
| DE | 10351150 A1 | 5/2005 |
| EP | 0623349 A1 | 11/1994 |
| EP | 1374923 A2 | 1/2004 |
| EP | 1470829 A1 | 10/2004 |
| JP | 2007-510446 A | 4/2007 |
| JP | 2009-500130 A | 1/2009 |
| JP | 2010-516307 A | 5/2010 |
| WO | 2005037447 A1 | 4/2005 |
| WO | 2005042045 A1 | 5/2005 |
| WO | 2008086794 A2 | 7/2008 |
| ZA | 200206983 A | 5/2003 |

OTHER PUBLICATIONS

EP Search Report issued Apr. 25, 2012 in EP Application No. 11009582.5.
Office Action issued Mar. 26, 2013 in CA Application No. 2,760,714.
English translation of an Office Action issued Oct. 15, 2013 in JP Application No. 2011-283030.
Office Action issued Feb. 4, 2014 in DE Application No. 10 2010 055 562.2.
Office Action issued Jan. 25, 2013 in AU Application No. 2011265339.

* cited by examiner

COATING DEVICE AND COATING METHOD

CROSS-REFERENCE TO RELATED APPLICATIONS

The present application claims priority to U.S. Provisional Patent Application No. 61/432,792, entitled "Coating Apparatus and Coating Process" and filed Jan. 14, 2011.

BACKGROUND OF THE INVENTION

The present invention relates generally to a device for coating a medical implant. The present invention also relates to a method for coating a medical implant using a device of the type.

The coating of medical implants with pharmaceutical agents has garnered increasing attention in the recent years. Antibiotic protection of the surface of implant materials is a central application of coating methods in this context. The improvement of the surface compatibility of medical implants that non-cemented medical implants in order to improve osseointegration is another important application.

Any implantation of articular endoprostheses, and of osteosynthesis materials as well, is associated with a certain risk of microbial contamination. Successful colonisation of microbial pathogens on the surface of the implant can lead to the manifestation of post-operative osteitis/osteomyelitis. Osteitis/osteomyelitis is a severe complication for the patient and, in addition, associated with substantial costs.

Gentamicin-doped PMMA bone cement has been in clinical use with cemented articular endoprostheses for decades with much success. The broadband antibiotic, gentamicin, contained in the bone cement protects the surface of the bone cement effectively from bacterial infections.

With regard to non-cemented articular endoprostheses and osteosynthesis materials, a number of approaches has been proposed in order to also attain local antibiotic protection of the implant surfaces.

For example, the use of poorly water-soluble antibiotic salts has been described in several patent specifications. For exemplary purposes, EP 0 623 349 A1, EP 1 470 829 A1, EP 1 374 923 A2, DE 101 42 465 A1, and DE 44 04 018 A1 can be cited in this context. The poorly water-soluble salts dissolve while releasing the antibiotics contained therein as a result of the action of body fluids. Prolonged release of the agent is advantageous. However, the laborious production of the salts is disadvantageous.

Alternatively, it is feasible to use water-soluble antibiotic salts. This is associated with a problem related to fixation of the antibiotic on the implant surface.

The majority of coatings that have been described thus far is preferably intended for the manufacture of coated implants under industrial conditions. This means that the industrial coating of the implants can only involve few agents that are relevant for large-scale use in order to be able to guarantee that the industrial manufacture is economic through sufficiently large throughput.

In particular in the case of antibiotic coatings, though, considering the increasingly problematic resistance status and the ensuing increased manifestation of multi-resistant pathogens, such as MRSA and MRSE, it is of interest to use antibiotics or combinations of antibiotics, which are specifically adapted to the germ at hand, for the coating of revision prostheses in one-stage or two-stage septic articular endoprosthesis replacement in order to ensure effective initial antibiotic protection of the implant surfaces.

It is also disadvantageous in this context that the methods for coating of medical implants are relatively laborious. Variable short-term application is not feasible. Various applications then require the stock-keeping of various coated medical implants in order to meet the needs of the different patients. This requires extensive stock-keeping and prevents uncommon mixtures for specific cases.

BRIEF SUMMARY OF THE INVENTION

It is an objective of a preferred embodiment of the present invention to overcome the disadvantages of the prior art. In particular, a simple and easy-to-use device and a method are to be provided that can be used to coat a surface of a medical implant, such as a prosthesis, without interfering with an ongoing surgery (OR). The aim is to be able to coat as many different medical implants as possible using the same device and the same method. Moreover, the device and the method should be variable to use such that they can be adapted to the medical needs, in particular to a suitable medication for the patient. The cleanliness required in operating theatres is another factor to take into account.

It is also an objective of a preferred embodiment of the present invention to develop a coating device that is as simple as possible and a coating method that is as simple as possible and can be used by the OR staff during an ongoing surgery, with the least time expenditure, to coat very different implants from any manufacturers with pharmaceutical preparations. It should further be feasible in this context to coat implants from any manufacturers under OR conditions with little effort using any liquid pharmaceutical preparations. Moreover, the device itself should not release any plastic particles, metal particles or any other particles that are not or only partly biodegradable. Another objective is that the device should, in particular, be suitable for the coating of non-cemented articular endoprostheses and osteosynthesis materials. Moreover, a coating procedure that is as simple as possible is to be developed.

The objective of a preferred embodiment of the present invention is met in that the device comprises a container that contains a liquid that comprises at least one pharmaceutically active substance, whereby the device comprises an elastic head for application of the liquid onto a surface to be coated that is connected to the inside of the container through at least one channel. Preferably, the surface to be coated is thus wetted by the liquid through contacting the surface to be coated, in particular by sweeping or rolling over it, and the elastic head.

According to a preferred embodiment of the present invention, a pharmaceutically active substance shall be understood to mean pharmaceutically effective means or means with a pharmacological effect as well as means that support a pharmacological effect or support in any other way the self-healing forces of the body. Examples include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

According to a preferred embodiment of the present invention, the term, liquid, also includes a viscous liquid. The width or cross-sections of the channels or channel can be adapted to the viscosity of the liquid for this purpose.

Moreover, a preferred embodiment of the present invention can provide the medical implant to be coated to be selected from hip endoprostheses, shoulder endoprostheses, elbow endoprostheses, marrow nails, and osteosynthesis plates.

A preferred embodiment of the present invention can also provide the liquid to comprise an aqueous solution of an antibiotic, preferably an aqueous gentamicin sulfate solution with a gentamicin sulfate content of 75.0 to 80.0% by weight. The gentamicin sulfate solution has an oily-viscous consistency and adheres very well to metal surfaces.

In this context, a preferred embodiment of the present invention can further provide that common pharmaceutical stabilisers are contained in the gentamicin sulfate solutions. These improve the durability and thus the usability of the liquid to be applied.

A preferred embodiment of the present invention can also provide for the use of other aminoglycoside antibiotic solutions such as aqueous solutions of tobramicin sulfate, amikacin sulfate, netilmicin sulfate, and sisomicin sulfate as liquid or components of the liquid. It is also feasible to use aqueous solutions of vancomycin, dalbavancin, ramoplanin, daptomycin, moxifloxacin, clindamycin, and lincomycin.

A particularly simple refinement of the invention provides the channels as intervening spaces of fibers, whereby the fibers form the elastic head. The refinement works according to the functional principle of a felt-tip pen, whereby the liquid containing the pharmaceutically active substance, rather than ink, is applied onto the medical implant. In this context, the fibers extend into the liquid or all of the liquid is contained in the fibers.

Moreover, the scope of a preferred embodiment of the present invention can provide for the use of combinations of solutions of different antibiotics as liquid. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride.

A preferred embodiment of the present invention can further provide for antiseptics solutions to be used as liquid, in particular solutions of chlorohexidine digluconate, octenidine dihydrochloride or polyhexanide.

According to a particularly advantageous refinement, a preferred embodiment of the present invention can provide the container to have elastic walls such that the liquid flows through the at least one channel to the surface of the elastic head upon a manual pressure being applied to the elastic container walls. What this achieves is that the amount of exiting liquid can be controlled through manual pressure.

Methods according to a preferred embodiment of the present invention can also be characterized in that the elastic head is a rotationally symmetrical roller that is supported as by a bearing at one end of the container such that the roller can rotate about its symmetry axis.

Another refinement according to a preferred embodiment of the method of the present invention can provide the elastic head to be a sphere that is supported as by a bearing at one end of the container such that it can rotate about at least one axis. The elastic head being capable of rotation is particularly advantageous in that the liquid can be applied onto the medical implant essential without kinetic friction. This not only prevents abrasion of the elastic head and thus of bothersome particles on the medical implant, but also allows the transfer of liquid to the medical implant to be controlled particularly well through this measure. In this context, a preferred embodiment of the present invention can provide the sphere to be supported as by a bearing on one end of the container such as to be freely rotatable.

Moreover, a preferred embodiment of the present invention can provide at least one channel to be formed between the container wall and the elastic head. This is advantageous, in particular in the context of an elastic head being supported as by a bearing such that it can rotate, since liquid is transported from the container to the surface of the device through the rotation of the elastic head and is then transferable to the surface of the medical implant.

A preferred embodiment of the present invention can also provide that it is feasible to fill an antibiotic or mixture of antibiotics that is/are well-suited for the existing treatment scenario and is present in the liquid into the container. This measure allows for individual adaptation to the actual treatment scenario of the respective patient.

According to a particularly preferred refinement, a preferred embodiment of the present invention can provide the pharmaceutically active substance to contain antibiotics and/or organic antiseptic agents in a manner such that the coating to be generated contains a pharmaceutically active dose.

A preferred embodiment of the present invention can also provide the elastic head to comprise a porous elastic sponge. According to a preferred embodiment of the present invention, the porous elastic sponge can be used to apply the liquid onto the medical implant in the form of a homogeneous film.

Another refinement of a preferred embodiment of the present invention proposes the elastic head to be arranged in the container in a manner such that it can be shifted linearly. In particular, a preferred embodiment of the present invention can provide that the elastic head can be pushed into the container. This pushes the liquid from the inside of the container outwardly when the elastic head is being pressed onto a surface.

A preferred embodiment of the present invention can also provide a channel to be provided in the elastic head, preferably through pores of a sponge.

Moreover, a preferred embodiment of the present invention can provide an inelastic plug to be arranged on the elastic head that closes the container on one side and comprises at least one channel and/or forms at least one channel between the plug and the container, whereby the plug preferably is arranged in the container in a manner such that it can be shifted linearly. This ensures the stability of the device.

Another refinement of a preferred embodiment of the present invention provides the elastic head to have a rough surface, preferably to have a roughness of 0.5 μm to 100 μm, particularly preferably of 1 μm to 10 μm, more particularly preferably 2 μm. In the case of an elastic head supported as by a bearing such that it can rotate, this supports stable conveyance of liquid to the surface of the device and thus onto the medical implant.

For this purpose, a preferred embodiment of the present invention can further provide the elastic head to be hydrophilic and the liquid to be an aqueous solution.

In order to meet the special hygiene requirements, a preferred embodiment of the present invention can provide the elastic head to close the container with respect to the outside except for the connection through the at least one channel.

In order to ensure that the container is easy to use and fill, the invention can provide the floor and/or at least one wall of the container to comprise, at least over regions thereof, an elastic membrane that can be perforated, whereby the membrane preferably is formed from a biocompatible elastomer and/or can be covered and/or sealed through a lid.

A preferred embodiment of the present invention can also provide the device to comprise a bearing for the elastic head that is connected to the container or is provided to be the same part as the container.

Particularly advantageous refinements of a preferred embodiment of the present invention provide the elastic head to have a modulus of elasticity of less than 2,000 MPa, preferably less than 500 MPa, particularly preferably between 1 and 100 MPa. With the modulus of elasticity values, the liquid can be applied to surfaces even in the case of uneven medical implant surfaces to be coated, when the device according to the invention is operated by hand.

A preferred embodiment of the present invention can also provide at least one channel, preferably all channels, to have a cross-section of less than 500 μm, preferably a cross-section of less than 200 μm.

Moreover, a preferred embodiment of the present invention can provide at least one channel to be a gap with a width of less than 500 μm, preferably with a width of less than 200 μm, preferably all channels to be the gaps. At the channel cross-sections and/or channel widths, a liquid film that is particularly well-suited for the medical purpose is applied.

A preferred embodiment of the present invention can also provide the elastic head and/or the container to comprise a biocompatible material, preferably at least the surface of the elastic head to consist of a biocompatible elastomer or elastomer mixture.

S preferred embodiment of the present invention can also provide the elastic head and/or the container to be manufactured from a biocompatible material.

A refinement of the device according to a preferred embodiment of the present invention that is particularly well to handle results, if the present invention provides the volume enclosed by the container and the elastic head to be between 0.5 ml and 1,000 ml, preferably between 1 ml and 100 ml.

a preferred embodiment of the present invention can also provide the container to contain sterile air or a sterile gas.

Moreover, a preferred embodiment of the present invention can provide at least one open-pore porous layer to be arranged between the elastic head and the container, preferably on the inside of the device. The open-pore porous layer is meant to ensure that there is always sufficient liquid present in the region of the elastic head.

Another refinement of a preferred embodiment of the present invention provides the liquid to comprise an aqueous gentamicin sulfate solution, preferably comprising stabilisers, whereby, in particular, an aqueous gentamicin sulfate solution with a gentamicin sulfate content of 0.5 to 88% by weight is preferred.

In this context, a preferred embodiment of the present invention can provide the liquid to be a gentamicin sulfate solution with a gentamicin sulfate content of 10 to 88% by weight, particularly preferably a gentamicin sulfate solution with a gentamicin sulfate content of 80% by weight.

The objective of a preferred embodiment of the present invention is also met by a method for coating a medical implant that has a device whereby a medical implant is provided and the elastic head of the device is contacted.

In this context, a preferred embodiment of the present invention can provide the container of the device to be filled with a liquid, preferably through injecting the liquid through a wall and/or the floor of the container, in particular through a membrane. This measure allows for individual adaptation to the actual treatment scenario of the respective patient.

In this context, a preferred embodiment of the present invention can again provide for a lid to be taken off before the container is being filled with the liquid and/or a lid to be fastened, preferably above a puncturing site, after the container has been filled with liquid. The use of a lid is to meant to prevent inadvertent opening or perforation of the container wall and to re-seal the container after the container wall or the floor of the container has been punctured or opened, such that no contamination can enter into the container and the content of the device cannot contaminate the surroundings, for example, the OR theatre.

Methods according to a preferred embodiment of the present invention are carried out before inserting the medical implants. Accordingly, the methods proceed "ex vivo."

Moreover, a preferred embodiment of the present invention can provide that at least 50% of the surface of the medical implant, preferably at least 80%, particularly preferably at least 90% of the surface of the medical implant, are being coated.

A preferred embodiment of the present invention can also provide for the method to be repeated as often as required for complete coating of the medical implant surface to be coated to be attained. In particular in the context of coloration of the liquid and testing of the completeness of coating through the coloration, this is advantageous according to a preferred embodiment of the present invention in order to generate a sufficiently coated medical implant.

According to a preferred embodiment of the present invention, the device can be pre-filled with a solution or suspension comprising the at least one pharmaceutically active substance such that the OR staff can coat the implant instantaneously. In this context, it is advantageous that the time expenditure for the coating is in the range of but a few seconds and valuable OR time can thus be saved.

Alternatively, it is feasible to provide a non-pre-filled device with one or more pharmaceutically active substances right in the OR theatre through injection of a solution or suspension comprising the at least one pharmaceutically active substance. In the case of the antibiotic coating, this enables suitable selection of an antibiotic or combination of antibiotics based on the existing resistance status and thus ensures that the coating matches the antibiotic sensitivity pattern.

It is also feasible to fill non-pre-filled devices with suitable solutions or suspensions of active substances in the respective hospital pharmacy prior to surgery such that coating can be carried out during the surgery without any time delay.

Examples of pharmaceutically active substances that can be used include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

Aminoglycoside antibiotic solutions such as aqueous solutions of tobramycin sulfate, amikacin sulfate, netilmicin sulfate, and sisomycin sulfate can also be used as antibiotics. It is also feasible to use aqueous solutions of vancomycin, dalbavancin, ramoplanin, daptomicin, moxifloxacin, clindamycin, and/or lincomycin. The use of combinations of solutions of various antibiotics is also included in the scope of a preferred embodiment of the present invention. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride. Moreover, it is feasible to use antiseptic agent solutions in place of antibiotic solutions. Examples include solutions of chlorohexidine gluconate, octenidine dihydrochloride or polyhexanide.

The scope of a preferred embodiment of the present invention also includes the use of solutions of antibiotics and antiseptic agents that contain, as solvents, organic solvents or combinations of organic solvents or combinations of organic solvents and water.

This allows, for example, poorly water-soluble antibiotic salts, such as laurates, myristates, palmitates, and stearates, to be used as well. Moreover, poorly water-soluble antibiotics or antibiotic salts in the form of suspensions can also be used.

A preferred embodiment of the present invention further provides the device as a drug or medical product.

A combination of the device according to a preferred embodiment of the present invention and a medical implant could be offered as well. The combination is formed by the device and the implant, whereby the combination has a minimal service life of 0.1 seconds. The combination arises during the coating process.

A preferred embodiment of the present invention is based on the surprising finding that a liquid to be used to coat a medical implant can be applied even shortly before its use through contacting, preferably by sweeping a device according to the invention, in which the liquid is stored, over the medical implant. The simple method and the device therefore ensure the usability in the OR as well. For this purpose, the liquid to be applied, which contains the pharmaceutically active substance, can be transported to an elastic head of the device through a channel, or better through multiple channels. In this context, according to a preferred embodiment of the present invention, the head being elastic ensures that the shape of the head adapts at least slightly to the external contours of the object to be coated. Mainly this surprising insight ensures the easy handling of the device according to the invention.

A particularly interesting refinement of a preferred embodiment of the present invention, in particular from the point of view of hygiene, is based on the additional aspect of a preferred embodiment of the present invention to provide the elastic head as a rotating roller or a sphere that can rotate freely in all directions. If the surface roughness of the roller or sphere is sufficient and/or sufficient wettability by the liquid is provided, the rotating elastic head conveys the liquid from the inside of the device to the surface to be coated. The liquid film is then applied much like with a deodorant stick without having to rub over the surface of the medical implant to be coated. The elasticity of the elastic head that is supported as by a bearing such that it can rotate should be such that the deformation is not propagated to the bearing of the elastic head in the container or if so, then only to a small degree such that the ability of the elastic head to rotate in the device is affected as little as possible. For this purpose, the container can comprise an elastic region in the region of the bearing.

For initial antibiotic protection, it is sufficient to have sufficiently high concentration(s) of antibiotic or antibiotics at the implant surfaces for a period of 24 to 72 hours. Therefore, sufficient temporary local antibiotic protection of the medical implant can be attained even upon local introduction of simple water-soluble antibiotics into a liquid.

Accordingly, rather than coating the medical implant much earlier during its manufacture, it can also be coated right before inserting it. This allows relatively short-acting coatings to be used as well. Moreover, even a layer that is still liquid can be used, which opens up new application fields and renders new active substances accessible.

A device according to a preferred embodiment of the present invention is designed such that no spray mist can contaminate the OR field and brushes, paint brushes or other components of a device releasing hairs or bristles or other particles are avoided.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Exemplary embodiments of the invention shall be illustrated in the following on the basis of two schematic figures, though without limiting the scope of the invention. In the figures.

DETAILED DESCRIPTION OF THE INVENTION

Figure 1:
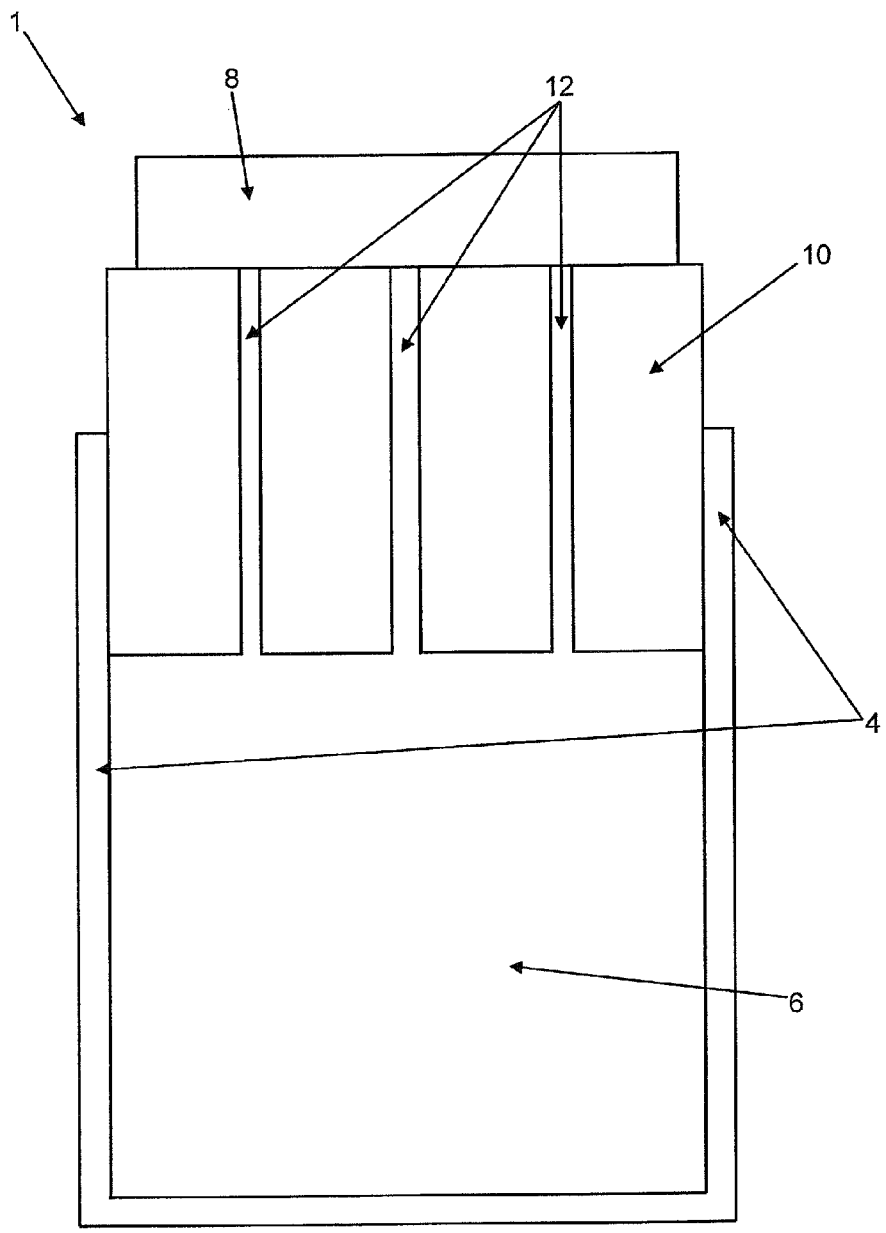
FIG. 1 is a schematic cross-sectional view of a device according to a preferred embodiment of the present invention.

Certain terminology is used in the following description for convenience only and is not limiting. The words "bottom," "upper" and "top" designate directions in the drawings to which reference is made. The word "outwardly" refers to a direction away from the geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIG. 1 shows a schematic cross-sectional view of a device 1 according to a preferred embodiment of the present invention. The device 1 preferably includes a container 4 in the form of a jar that is open on its top. The side walls of the container 4 are preferably cylindrical and of even thickness.

An aqueous liquid 6 that contains a pharmaceutically active substance is situated on the inside of the container 4. The liquid 6 is, for example, an aqueous solution containing antibiotics to be used for coating a medical implant (not shown).

An elastic head 8 in the form of a sponge 8 is arranged on a plug 10 in the opening of the container 4. The plug 10 is plugged into the opening of the container 4 and closes it on all sides. Multiple channels 12 are arranged in the plug 10 through which the liquid 6 is guided from the inside of the container 4 to the porous sponge 8. The sponge 8 is hydrophilic and thus well-suited for taking up the liquid 6. Accordingly, the sponge 8 can soak up the liquid 6 through the channels 12.

The plug 10 and the internal walls of the container 4 can consist of a hydrophobic material or be coated by a hydrophobic material. The plug 10 can be shifted in the opening of the container 4, for example, it is linearly mobile in the opening of the container, and is guided through the internal walls of the container 4.

The device 1 shown can be used to carry out a method according to a preferred embodiment of the present invention. For this purpose, the device 1 is swept over a surface of a medical implant to be coated with the elastic head 8 downward. The pressure applied to the sponge 8 squeezes the liquid 6 contained in the sponge 8 out and transfers it as a liquid film to the surface of the medical implant. The manually applied pressure simultaneously squeezes the liquid 6 from the inside of the container 4 into the sponge 8 such that replenishment of the liquid to the surface of the elastic head 8 is ensured. The liquid film dries quickly on the surface of the medical implant and leaves a layer of a pharmaceutically active substance, for example of an antibiotic or a mixture of antibiotics. The coated medical implant is then ready for use in a surgery, for example, is ready to be inserted.

In this context, the composition of the liquid 6 can be determined and established shortly before the surgery through adding suitable pharmaceutically active substances through the walls and/or floor of the container 4 using a syringe. Alternatively, prior to its use, the container 4 can simply be filled with a suitable liquid 6 through the opening of the container 4 before plugging the plug 10 into the opening. For this purpose, the container 4 and the plug 10 having the elastic head 8 can previously be stored in a sterile packaging, which may also be filled with a sterilizing gas. The container 4 itself may be filled with the sterilizing gas as well.

The coating device 1 is manufactured from polypropylene, has a height of approximately 20 cm and a diameter of 8 cm. The plug 10 also consists of polypropylene and is inserted in a press-fit into the upper region of the internal space of the container 4. Before its use, the container 4 can be closed in a germ-tight manner through an aluminum compound foil (not shown) that closes the opening of the container 4.

Figure 2:
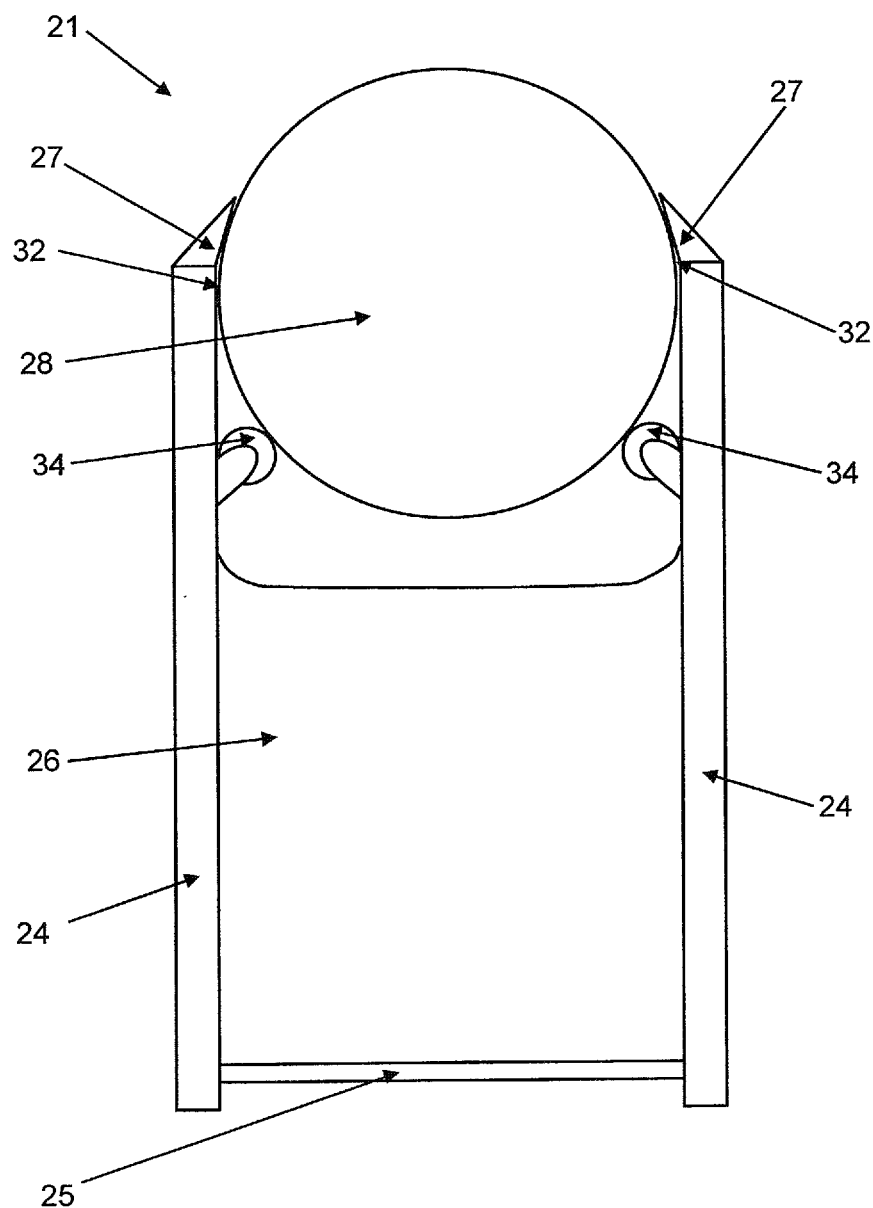
FIG. 2 is a cross-sectional view of a second device according to a preferred embodiment of the present invention.

FIG. 2 shows a schematic cross-sectional view of a second device 21 according to a preferred embodiment of the present invention that is suitable for a method according to a preferred embodiment of the present invention. The device 21 includes a container 24 with an bottom-side elastic membrane 25 that can be perforated that closes the container 24 on its underside completely. A liquid 26 containing a pharmaceutically active substance that is used to coat the medical implant when the solvent of the liquid, in which the pharmaceutically active substance is dissolved, is evaporated, is situated on the inside of the container 24. Syringes can be punctured through the membrane 25 in order to fill the container 24 with liquid 26 or in order to add the pharmaceutically active substance to the liquid 26 contained in the container 24.

A circumferential lip 27 made of an elastic material is arranged on the container walls at the top of the container 24. The top of the container 24 is closed through a sphere 28 as an elastic head 28 of the device 21. The sphere 28 is manufactured from an elastic biocompatible polymer and has a surface roughness of 10 μm. Between the sphere 28, the walls of the container 24, and the lip 27, there is a gap 32 that serves as channel 32 for the liquid 26 on the inside of the container 24.

The sphere 28 is supported as by a bearing in the container 24 through the lip 27 and through a ball bearing 34. This renders the sphere 28 freely mobile, i.e. it can rotate in all directions. The ball bearing 34 is not required for the refinement of a preferred embodiment of the present invention such that, rather, the sphere 28 can simply be supported as by a bearing to be gliding on a liquid film of the liquid 26 in a bracketing on the upper end of the container 24.

While rolling the device 21 with the sphere 28 downwards over a medical implant (not shown), the device conveys the liquid on its rough surface from the inside of the device 21 through the gap 32 to the external surface of the device 21 that is formed by the sphere 28. When the sphere 28 is pressed into the ball bearing 34 through the pressure from the weight of the device 21 and, if applicable, the user actuating the device 21, the gap 32 has a width of approximately 50 μm. However, the gap width can just as well be adapted to the consistency of the liquid 26 and/or the roughness of the sphere 28. The more viscous the liquid 26, the wider the gap 32 is selected to be.

If no ball bearing 34 is provided, channels, rather than the gap 32, can be arranged in the form of flat furrows in the bearing of the container that have a width of approximately 1 to 10 mm and a depth of 50 to 200 μm. The liquid 26 can then be transported from the device 21 in the channels. In the scope of a preferred embodiment of the present invention, the device 21 can just as well be provided such that the sphere 28 actually glides just on the liquid film that keeps being reproduced upon the rotation in the container 24. The sphere 28 must be provided to have sufficient surface roughness for this purpose.

The preferred embodiment according to the present invention according to FIG. 2 is special and corresponds to the scope of the present invention in that the liquid 26 contains a pharmaceutically active substance to be used for coating a medical implant, and in that the sphere 28 concurrently forms the elastic head 28 of the device 21, whereby the liquid 26 is conveyed from the inside of the device 21 through the rotation of the sphere 28 and whereby the liquid 26 is applied to surfaces even in the case of uneven contours of the medical implant owing to the elasticity of the sphere 28.

According to a preferred embodiment of the present invention, the liquid-filled devices 1, 21 can be swept briefly over customary Zweymüller hip endoprostheses. The Zweymüller hip endoprostheses are thus furnished with a film of a liquid 6, 26 at the surface of the stem. Once the liquid film dries up, the Zweymüller hip endoprostheses may show a white coating at the surface of the stem, in which the pharmaceutically active substance is contained. The hip endoprostheses are thus ready for use in a surgery.

Following the coating with a liquid 6, 26, the still wet medical implant can also be coated with a powder. The powder contains a second pharmaceutically active substance, preferably a bone growth-promoting substance, such as calcium phosphate. The liquid film on the medical implant causes the powder to adhere well to the surface thereof. This results in a liquid-powder coating on the medical implant surface to be coated.

Examples of the production of liquids for a method according to a preferred embodiment of the present invention and another example of a device according to a preferred embodiment of the present invention are illustrated in the following.

Example 1

Production of a Coating Solution Containing Gentamicin Sulfate

A total of 16.0 g gentamicin sulfate (Fujian Fukang Ltd) were mixed with 4.0 ml pyrogen-free sterile water at room temperature. After stirring with a magnetic stirrer for 24 hours at room temperature, an oily-viscous yellowish solution had formed. A coating solution containing gentamicin sulfate as liquid for coating a medical implant was thus obtained.

Example 2

Production of a Coating Solution Containing the Two-Component Combination of Gentamicin Sulfate and Clindamycin Hydrochloride A total of 12.0 g gentamicin sulfate (Fujian Fukang Ltd) were mixed with 4.0 g clindamycin hydrochloride (Sigma-Aldrich), and 4.0 ml pyrogen-free sterile water at room temperature. After stirring with a magnetic stirrer for 24 hours at room temperature, an oily-viscous yellowish solution had formed.

Example 3

Production of a Coating Solution Containing the Three-Component Combination of Gentamicin Sulfate, Clindamycin Hydrochloride, and Vancomycin Hydrochloride A total of 4.0 g gentamicin sulfate (Fujian Fukang Ltd) were mixed with 4.0 g clindamycin hydrochloride (Sigma-Aldrich), 4.0 g vancomycin hydrochloride (Sigma-Aldrich), and 8.0 ml pyrogen-free sterile water at room temperature. After stirring with a magnetic stirrer for 24 hours at room temperature, a viscous yellowish solution had formed.

Example 4

Production of a Coating Solution Containing the Two-Component Combination of Gentamicin Sulfate and Clindamycin Hydrochloride A total of 3.0 g gentamicin sulfate (Fujian Fukang Ltd) were mixed with 1.0 g clindamycin hydrochloride (Sigma-Aldrich), and 1.0 ml pyrogen-free sterile water at room temperature. After stirring with a magnetic stirrer for 24 hours at room temperature, an oily-viscous yellowish solution had formed.

Example 5

Production of a Coating Solution Containing the Three-Component Combination of Gentamicin Sulfate, Clindamycin Hydrochloride, and Vancomycin Hydrochloride A total of 2.0 g gentamicin sulfate (Fujian Fukang Ltd) were mixed with 1.0 g clindamycin hydrochloride (Sigma-Aldrich), 1.0 g vancomycin hydrochloride (Sigma-Aldrich), and 1.0 ml pyrogen-free sterile water at room temperature. After stirring with a magnetic stirrer for 24 hours at room temperature, a viscous yellowish solution had formed.

Examples 6-10

Production of a Coated Implant

Conventional 10 ml plastic syringes were used in each case to draw up the coating solutions of examples 1-5 and, after attaching a cannula, injected through the floor plate into the container of a device according to a preferred embodiment of the present invention.

The devices that were thus filled were applied by rolling onto customary Zweymüller hip prostheses. In the process, a viscous film formed on the implant surfaces.

The features of the present invention disclosed in the preceding description and in the claims, figures, and exemplary embodiments, can be essential for the implementation of the various embodiments of the invention both alone and in any combination.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for coating a medical implant, the device comprising:
   a container containing a liquid that comprises at least one pharmaceutically active substance, the container having a first end, a second end having a bottom wall, and at least one container wall extending from the first end toward the second end, at least one region of at least one of the bottom wall and the container wall comprising an elastic membrane configured to be perforated; and
   an elastic head provided at the first end and in communication with an interior of the container through at least one channel,
   wherein the elastic head applies the liquid onto a surface of the medical implant.

2. The device according to claim 1, wherein the container is configured such that the liquid flows through the at least one channel to a surface of the elastic head upon application of a manual pressure to the container.

3. The device according to claim 1, wherein the elastic head is a sphere that is supported by a bearing at the first end of the container such that the elastic head is rotatable about at least one axis.

4. The device according to claim 1, wherein the at least one channel is formed between the container wall and the elastic head.

5. The device according to claim 1, wherein the elastic head comprises a porous elastic sponge and the at least one channel is formed in the elastic head through pores of the sponge.

6. The device according to claim 1, wherein an inelastic plug is arranged on the elastic head, closes the container at the first end, and comprises the at least one channel or forms the at least one channel between the plug and the container, whereby the plug is arranged in the container in a manner such that the plug can be shifted linearly.

7. The device according to claim 1, wherein the elastic head has a surface roughness of 1 μm to 10 μm.

8. The device according to claim 1, wherein the elastic head is hydrophilic and the liquid is an aqueous solution.

9. The device according to claim 1, wherein the elastic head has a modulus of elasticity between 1 and 100 MPa.

10. The device according to claim 1, wherein the at least one channel has a cross-section of less than 200 μm.

11. The device according to claim 1, wherein at least one open-pore porous layer is arranged between the elastic head and the container on an inside of the device.

12. The device according to claim 1, wherein the liquid comprises an aqueous gentamicin sulfate solution with a gentamicin sulfate content of 0.5 to 88% by weight.

13. The device according to claim 1, wherein the at least one channel is provided as intervening spaces of fibers, whereby the fibers form the elastic head.

* * * * *